United States Patent
Perler

(10) Patent No.: US 8,668,743 B2
(45) Date of Patent: Mar. 11, 2014

(54) PROSTHETIC DEVICE WITH MULTI-AXIS DUAL BEARING ASSEMBLY AND METHODS FOR RESECTION

(76) Inventor: Adam D. Perler, Carmel, IN (US)

( * ) Notice: Subject to any disclaimer, the term of this patent is extended or adjusted under 35 U.S.C. 154(b) by 15 days.

(21) Appl. No.: 13/286,760

(22) Filed: Nov. 1, 2011

(65) Prior Publication Data

US 2012/0109326 A1   May 3, 2012

Related U.S. Application Data

(60) Provisional application No. 61/409,280, filed on Nov. 2, 2010.

(51) Int. Cl.
*A61F 2/42* (2006.01)

(52) U.S. Cl.
USPC ........................................................ 623/21.18

(58) Field of Classification Search
USPC ................. 623/20.29, 20.33, 21.11–21.19
See application file for complete search history.

(56) References Cited

U.S. PATENT DOCUMENTS

| | | | |
|---|---|---|---|
| 3,975,778 A | 8/1976 | Newton, III | |
| 4,232,404 A | 11/1980 | Samuelson et al. | |
| 4,755,185 A | 7/1988 | Tarr | |
| 4,759,766 A | 7/1988 | Buettner-Janz et al. | |
| 5,314,485 A | 5/1994 | Judet | |
| 5,326,365 A | 7/1994 | Alvine | |
| 5,766,259 A | 6/1998 | Sammarco | |
| 5,824,106 A | 10/1998 | Fournol | |
| 6,039,763 A | 3/2000 | Shelokov | |
| 6,183,519 B1 | 2/2001 | Bonnin et al. | |
| 6,258,126 B1 | 7/2001 | Colleran | |
| 6,409,767 B1 | 6/2002 | Perice et al. | |
| 6,663,669 B1 | 12/2003 | Reiley | |
| 6,699,295 B2 | 3/2004 | Lee et al. | |
| 6,764,521 B2 | 7/2004 | Molino et al. | |
| 6,852,130 B2 | 2/2005 | Keller et al. | |
| 6,860,902 B2 | 3/2005 | Reiley | |
| 6,926,739 B1 | 8/2005 | O'Connor et al. | |
| 6,939,380 B2 | 9/2005 | Guzman | |
| 7,011,687 B2 | 3/2006 | Deffenbaugh et al. | |
| 7,025,790 B2 | 4/2006 | Parks et al. | |
| 7,323,012 B1 | 1/2008 | Stone et al. | |

(Continued)

OTHER PUBLICATIONS

M.P. Jackson et al., Total Ankle Replacement, Current Orthopedics, 17, pp. 292-298, 2003, Elsevier Ltd., UK.

(Continued)

*Primary Examiner* — Thomas J Sweet
*Assistant Examiner* — Megan Wolf
(74) *Attorney, Agent, or Firm* — Bruce J. Bowman

(57) ABSTRACT

An orthopedic prosthesis, system and method has a dual bearing component that, along with first and second bone anchoring components, provides multi-axial movement separately with respect to both the first and second bone anchoring components. An ankle prosthesis, system and method may thus be fashioned utilizing these principles that includes a dual bearing component, a tibial component adapted for attachment to the tibia bone, and a talar component adapted for attachment to the talus or calceneus bone of the foot. The dual bearing component includes a superior bearing providing gliding articulation/translation between it and the tibial component, and an inferior bearing providing gliding articulation/translation between it and the talar component. A bearing component plate provides a base or foundation for the superior and inferior bearings. The superior bearing is bonded to the bearing component plate while the inferior bearing moves with respect to the bearing component plate.

30 Claims, 11 Drawing Sheets

(56) References Cited

U.S. PATENT DOCUMENTS

| | | | |
|---|---|---|---|
| 7,351,261 B2 | 4/2008 | Casey | |
| 7,481,840 B2 | 1/2009 | Zucherman et al. | |
| 7,534,246 B2 | 5/2009 | Reiley et al. | |
| 7,534,270 B2 | 5/2009 | Ball | |
| 7,597,713 B2 | 10/2009 | Baumgartner et al. | |
| 7,625,409 B2 | 12/2009 | Saltzman et al. | |
| 7,713,305 B2 | 5/2010 | Ek | |
| 7,717,920 B2 | 5/2010 | Reiley | |
| 2004/0030399 A1 | 2/2004 | Asencio | |
| 2004/0133278 A1* | 7/2004 | Marino et al. | 623/17.14 |
| 2004/0167631 A1 | 8/2004 | Luchesi et al. | |
| 2004/0186585 A1 | 9/2004 | Feiwell | |
| 2005/0004676 A1 | 1/2005 | Schon et al. | |
| 2005/0182492 A1 | 8/2005 | Pappas et al. | |
| 2005/0203629 A1 | 9/2005 | Cipolletti et al. | |
| 2005/0288792 A1 | 12/2005 | Landes et al. | |
| 2006/0020345 A1 | 1/2006 | O'Connor et al. | |
| 2006/0142870 A1 | 6/2006 | Robinson et al. | |
| 2006/0167559 A1 | 7/2006 | Johnstone et al. | |
| 2006/0247788 A1 | 11/2006 | Ross | |
| 2007/0027547 A1 | 2/2007 | Rydell et al. | |
| 2007/0112431 A1 | 5/2007 | Kofoed | |
| 2007/0173944 A1* | 7/2007 | Keller et al. | 623/18.11 |
| 2007/0225823 A1 | 9/2007 | Hawkins et al. | |
| 2008/0097617 A1 | 4/2008 | Fellinger et al. | |
| 2008/0103603 A1 | 5/2008 | Hintermann | |
| 2008/0215156 A1* | 9/2008 | Duggal et al. | 623/18.11 |
| 2009/0182433 A1 | 7/2009 | Reiley et al. | |
| 2009/0240338 A1 | 9/2009 | Reiley | |
| 2010/0198355 A1 | 8/2010 | Kofoed et al. | |
| 2010/0204799 A1 | 8/2010 | Keller et al. | |
| 2010/0241237 A1 | 9/2010 | Pappas | |
| 2010/0268337 A1 | 10/2010 | Gordon et al. | |
| 2010/0305572 A1 | 12/2010 | Saltzman et al. | |

OTHER PUBLICATIONS

A. Younger et al, Mobile-Bearing Total Ankle Arthroplasty, Foot and Ankle Clinics N Am, #13, pp. 495-508, 2008, Elsevier Inc., US.

M. S. Myerson et al, Primary and Revision Total Ankle Replacement Using Custom-Designed Prostheses, Foot and Ankle Clinics N. Am, #13, pp. 521-538, 2008, Elsevier Inc., US.

S. Giannini et al., The BOX Total Ankle Arthroplasty, Foot and Ankle, Chapter 113, pp. 1-10, US, 2011.

W. Eisner, FDA Ortho Panel Recommends STAR Ankle PMA Approval—With Elephant in the Room, Orthopedics This Week, vol. 3, Issue 15, pp. 9-12, Ry Publications, Wayne, PA, US, 2007.

D. Paley et al, Ankle Joint Disraction, Foot and Ankle Clinics N Am, #10, pp. 685-698, 2005, Elsevier Inc., US.

Summary Minutes of the Meeting of the Orthopaedic and Rehabilitation Devices Panel, pp. 1-22, Apr. 24, 2007, US.

P. F. Rippstein, Clinical Experiences With Three Different Designs of Ankle Prostheses, Foot and Ankle Clinics N Am, #7, pp. 817-831, 2002, Elsevier Science, US.

D. Rodriguez et al., Medium Term Follow-up of the AES Ankle Prothesis: High Rate of Asymptomatic Osteolysis, Foot and Ankle Surgery, #16, pp. 54-60, 2010, Elsevier Ltd., UK.

Tornier Ankle Implants, Mar. 17, 2009, pp. 1-5.

P. Yalamanchili et al., Salto Talaris Total Ankle Replacement, Operative Techniques in Orthopaedics, #18, pp. 277-281, 2008, Elsevier Inc., US.

S. Schill et al., Endoprothetik am rheumatischen oberen Sprunggelenk, FussSprungg, #4, pp. 98-105, 2006, Germany.

S. Raikin et al., Mobility Characteristics of Total Ankle Replacements, Orthopedic Research Laboratories, Lutheran Hospital, Cleveland Clinic Health System, pp. 1-6, 2000, Cleveland, Ohio, US.

S. Siegler et al., Mechanics of the Ankle and Subtalar joints Revealed Through a 3D Quasi-static Stress MRI Technique, Journal of Biomechanics, #38, pp. 567-578, 2005, Elsevier Ltd., UK.

STAR Ankle IDE Summary Outcomes Data, Orthopedic and Rehabilitation Devices Advisory Panel Meeting, Apr. 24, pp. 1-10, 2007.

Y. Tochigi et al., The Effect of Accuracy of Implantation on Range of Movement of the Scandinavian Total Ankle Replacement, The Journal of Bone & Joint Surgery (Br), #87-B, pp. 736-740, 2005, British Editorial Society of Bone and Joint Surgery, UK.

H. Ohgushi et al., Tissue Engineered Ceramic Artificial Joint—ex vivo Osteogenic Differentiation of Patient Mesenchymal Cells on Total Ankle Joints for Treatment of Osteoarthritis, Biomaterials, #26, pp. 4654-4661, 2005, Elsevier Ltd, UK.

K. Watanabe, et al., Analysis of Joint Laxity After Total Ankle Arthroplasty: Cadaver Study, Clinical Biomechanics, #24, pp. 655-660, 2009, Elsevier Ltd., UK.

International Search Report (ISR) and the Written Opinion of the International Searching Authority for PCT/US2011/058883, PCT International Searching Authority, Feb. 8, 2012, 7 pages.

* cited by examiner

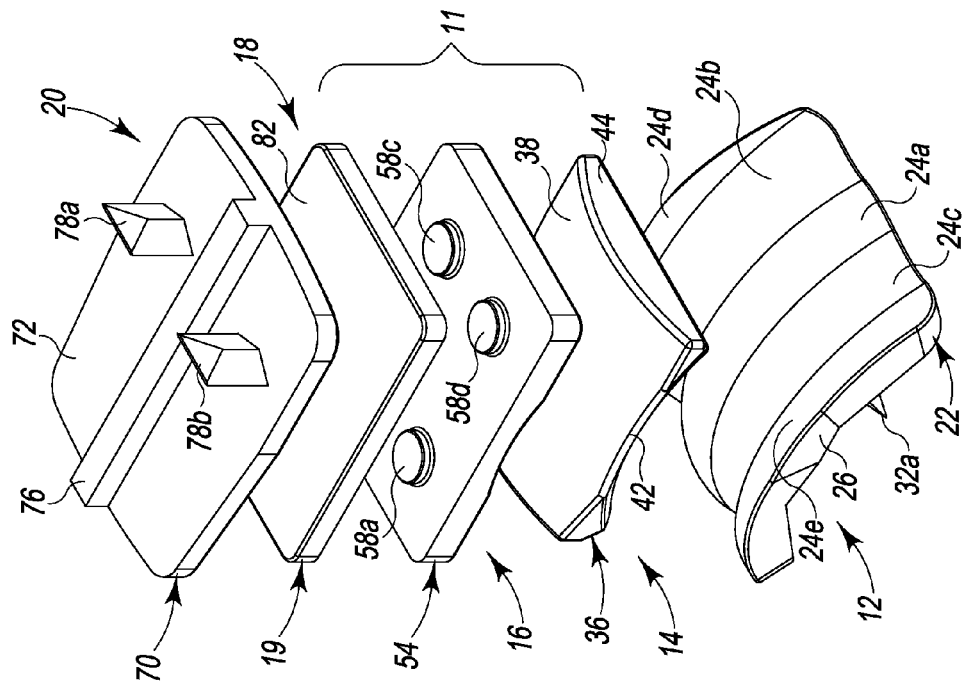
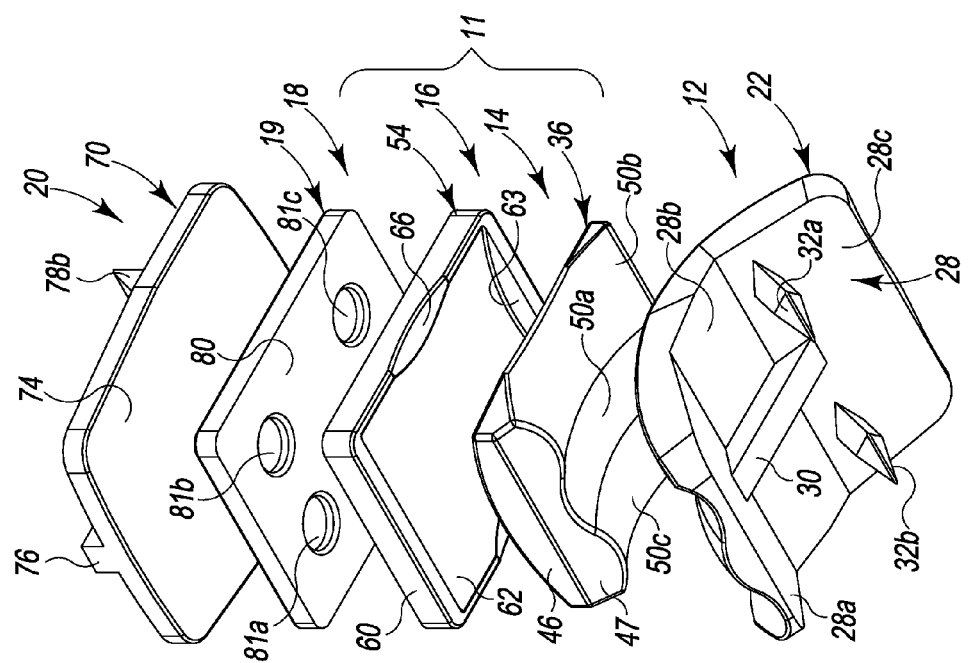
Fig. 8
Fig. 7

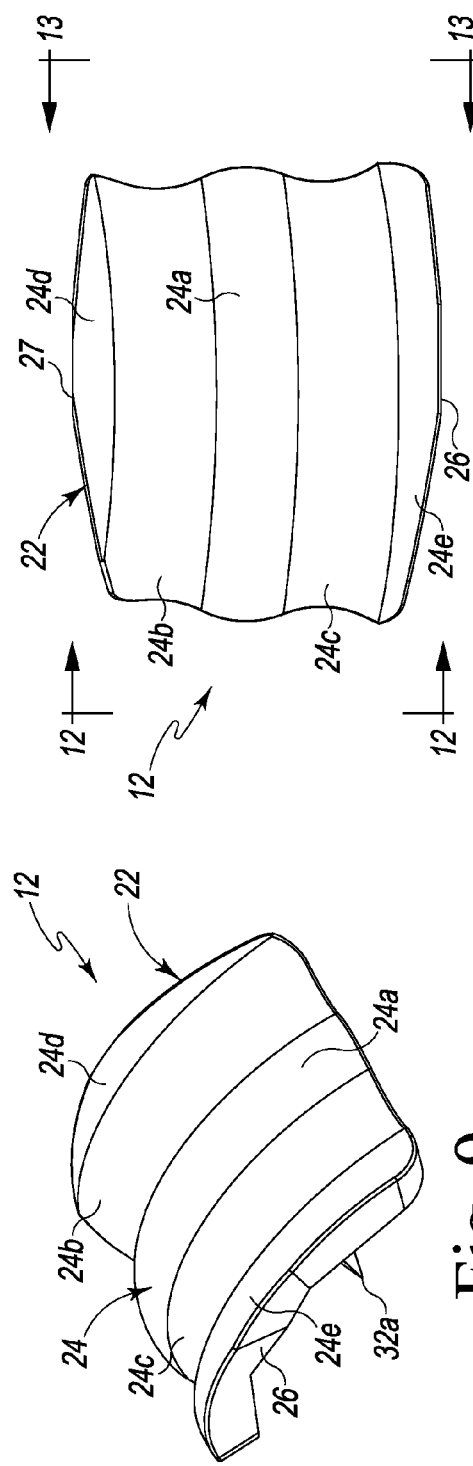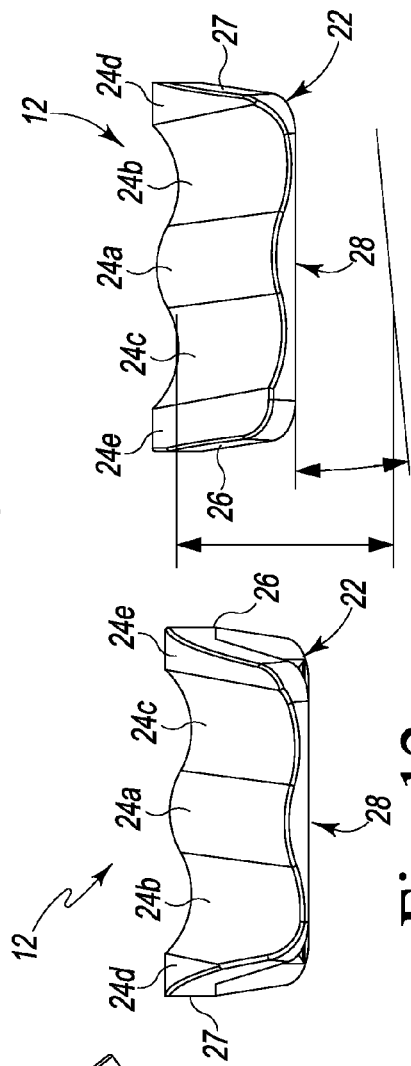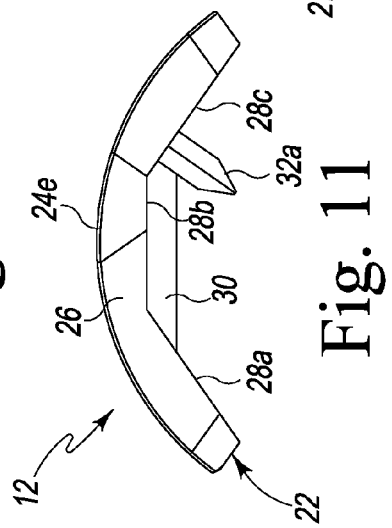
Fig. 9
Fig. 10
Fig. 11
Fig. 12
Fig. 13

PROSTHETIC DEVICE WITH MULTI-AXIS DUAL BEARING ASSEMBLY AND METHODS FOR RESECTION

RELATED APPLICATIONS

This patent application claims the benefit of and/or priority under 35 U.S.C. §119(e) to U.S. Provisional Patent Application Ser. No. 61/409,280 filed Nov. 2, 2010, entitled "Prosthetic Device with Multi-Axis Dual Bearing Assembly and Methods for Resection" the entire contents of which is specifically incorporated herein by this reference.

BACKGROUND OF THE INVENTION

1. Field of the Invention

The present subject matter is directed generally to orthopedic prostheses, joint replacement systems and methods and, more particularly, to a multi-axis mobile bearing prosthesis, system and method for implantation.

2. Background Information

The concept of total ankle arthroplasty has a long and relatively unsuccessful history due to the high failure rate often associated with the original implant devices and implantation techniques. Only recently has total ankle arthroplasty regained some recognition as a viable treatment for limited indications and as a viable alternative to an ankle joint fusion, which is often referred to as the gold standard of treatment. It has been shown that replacement of an ankle joint with an ankle prosthesis can be particularly challenging due to the relatively small articular contact surfaces of the ankle, complex biomechanics of both the ankle and hindfoot joints, limited and risky access to the ankle joint during replacement, and wide variation in patient candidacy. Past flawed design rationale and the above factors have led to a high rate of post-operative complications such as loosening of the ankle prosthesis, subsidence, pain, abnormal ankle prosthesis wear, and/or meniscal/bearing breakdown—often leading to ankle implantation failure.

In addition to the technical difficulties, regulatory agencies have classified ankle prosthetics in a manner which is often viewed as substantially limiting scientific progress in the field of ankle replacement due to the financial burden of obtaining market clearance for such devices.

Currently, two classes of ankle prosthetics are generally available; a semi-constrained ankle prosthetic and an unconstrained ankle prosthetic. Both types of ankle prosthetics utilize either a three (3) piece and two (2) component design (with the meniscal portion/bearing locking into the tibial plate) or a three (3) piece and three (3) component design (with a mobile/unlocked bearing) including an upper, middle, and lower component (tibial, bearing, and talar component, respectively).

A semi-constrained ankle prosthesis typically provides a tibial fixation component (usually metal) which provides firm attachment to the distal end of the tibia bone. A talar component provides firm attachment to the superior surface of a prepared talus, and provides on its upper or proximal side a surface for articulation. A bearing component can fit between the tibial component and the talar component and is typically locked/fixed to the tibial component. The underside of the bearing can provide a surface to articulate with the surface of the talar component. These surfaces can be structured such that all motions present in a normally aligned ankle joint can be at least partially replicated. Such motions can include plantar/dorsiflexion, rotation about the tibial/talar axis, some medial/lateral translation, and some anterior/posterior translation. Rotations in the frontal plane or motion in the transverse plane are usually not well supported as there is little curvature in this region. The influence of the subtalar joint axis of motion is not generally taken into consideration with this type of device, which can alter the function and position of the talar body and therefore the talar component. These motions can occur actively and lead to edge loading, causing higher stress and greater propensity for wear. Also, as the articular surfaces can be designed for mismatch, even under optimum implant positioning and loading, higher stress will be seen at the contact point due to the point loading associated with mismatched radii of the articular surfaces as the surface contact areas are smaller and thus experience much greater loads.

Unconstrained prosthetics are all generally the same in function. They are similar to semi-constrained prostheses except that the potential for motion between the tibial component and the bearing component is designed into the prosthesis with anterior to posterior rotation of the ankle in the sagittal plane and gliding motion in the transverse plane. There is not intimate fit between the bearing component and the tibial component as the tibial component usually has a flat undersurface and the bearing component usually has a simple flat upper surface so that translation and rotation are allowed at this interface. Further, the interface between the talar component and the bearing component can have a curvature that is matched, so there is a large contact surface area and optimized contact stress that can result in reduced wear. This matched articulation can be accomplished because other motions are allowed for between the tibial and bearing components. It has been clearly shown with clinical history in all joints that if these motions are not allowed for, the force must be absorbed at the implant bone interface, and can lead to a greater propensity for loosening. The current systems in this category do not often address the frontal plane motion influence of the underlying subtalar joint axis.

Therefore, it is apparent from the above that the need exists for multi-axis dual mobile bearing joint prostheses.

Additionally, current methods of bone surface preparation, such as resection of the tibia and talus bone for ankle joint prosthesis implantation, typically involve using a hand-held bone saw that is held by the surgeon for making the resection cut. These methods of bone resection have several disadvantages including over-cutting of the resection of the bone surfaces, initial misalignment of the cut, performing cuts that are not straight throughout the length of the cut, and lack of reproducibility. These disadvantages often lead to longer healing time and/or more pain for the patient, performance problems of the prosthesis due to malalignment, or improper contact between the implant components and the resected bone surfaces.

Moreover, current methods of bone surface preparation and prosthesis implantation as they relate to ankle joint replacement typically include an anterior to posterior approach and implantation procedure. This approach can suffer from numerous potential complications such as a potential for the disruption of blood supply, restricted bone access, damage to the neurovascular bundle anterior and posterior to the ankle, extensive scarring and soft tissue adhesions, improper posterior joint resection, and the larger amount of bone resection often involved.

Therefore, the need exists for systems and methods of bone surface preparation for prosthesis implantation that address the aforementioned problems and leads to a more reproducible outcome.

SUMMARY OF THE INVENTION

The present invention is a multi-axis dual bearing orthopedic prosthesis, system and methods of joint prosthesis implantation. A dual bearing component of the orthopedic prosthesis, along with first and second bone anchoring components, provides multi-axial and independent movement with respect to both the first and second bone anchoring components.

In one form, the multi-axial dual bearing orthopedic prosthesis is fashioned as an ankle prosthesis. The ankle prosthesis includes a dual bearing component, a tibial component adapted for attachment to a tibia or fibula bone, and a talar component adapted for attachment to a talus or calceneus bone of the foot. The dual bearing component includes a superior bearing providing gliding articulation/translation between it and the tibial component, and an inferior bearing providing gliding articulation/translation between it and the talar component.

The dual bearing component may include a bearing component plate that provides a base or foundation for the superior and inferior bearings. The superior bearing is bonded to the bearing component plate while the inferior bearing moves with respect to the bearing component plate.

Particularly, the talar component has an inferior surface with a bone fixation portion for fixation to a talus or calceneal bone and a superior surface designed for articulation with the inferior bearing of the bearing component. The inferior bearing of the bearing component articulates with the superior surface of the talar component through congruent complimentary articulating surfaces provided on the two. The tibial component has a superior surface with a bone fixation portion for fixation to the tibia bone or a fibula bone, and an inferior surface for articulation with the superior bearing of the bearing component through smooth surfaces of the two.

More particularly, the ankle prosthesis includes a talar component having inferior surface with a bone fixation portion for fixation to the talus bone and/or calceneus (in the event of a non-viable talar bone) and a superior surface designed for articulation with a polyaxial mobile bearing component. The polyaxial mobile bearing component has an inferior surface for articulation with the talar/calcaneal component and a separate superior surface designed for articulation with a tibial component. The tibial component has an inferior surface for articulation with the polyaxial mobile bearing component and a superior surface with a bone fixation portion for fixation to a tibia bone and/or a fibula bone.

The polyaxial mobile bearing component has a smooth superior surface adapted for gliding on a smooth inferior surface of the tibial component to allow desired rotational and translational movements. The polyaxial mobile bearing component has a contoured inferior surface that is mostly congruent with the a contoured superior surface of the talar component which allows for frontal plane motion, but limits the transverse and sagital plane motion. The inferior surface has a proximal surface that is mostly congruent with a distal aspect of the proximal bearing while the distal aspect of the inferior surface is mostly congruent with the superior surface of the talar component and allows for mostly sagital plane rotation/motion/excursion.

A method and system are provided that is used to prepare a bone surface for the implantation of a prosthesis fashioned in accordance with the present principles includes determining a location for a linear cut line on the bone surface and drilling a series of furrows tangent to the linear cut line to create an environment conducive to bone integration with the prosthesis.

With respect to the present ankle prosthesis, a method and system for implantation thereof includes the use of a lower extremity alignment guide, tibial and talar drill guides, tibial and talar saw guides, and tibial and talar broach guides, all components of which can be placed on and removed from multiple alignment anchor pins throughout the implantation procedure. Methods include an anterior implantation via an anterior implantation device, and a lateral to medial or medial to lateral implantation via a lateral to medial or medial to lateral implantation device. The methods include exposing the tibia and talus bones from the anterior (the anterior implantation method), from the lateral (or medial) side, resection of the tibia and talus bones, broaching the tibia and talus bones, and positioning and affixing the ankle joint prosthesis components.

It is therefore an object of the present invention to provide a novel multi or poly axial orthopedic prosthesis, system and method, and systems and methods for bone resection and prosthetic implantation.

BRIEF DESCRIPTION OF THE DRAWINGS

The above mentioned and other features, advantages and objects of this invention, and the manner of attaining them, will become apparent and the invention itself will be better understood by reference to the following description of the invention taken in conjunction with the accompanying drawings, wherein:

FIG. 7 is an exploded isometric inferior view of the right ankle prosthesis of FIG. 1 from a posterior/lateral viewpoint;

FIG. 8 is an exploded isometric superior view of the right ankle prosthesis of FIG. 1 from an anterior/lateral viewpoint;

FIG. 9 is an isometric superior/lateral view of a talar component of the right ankle prosthesis of FIG. 1;

FIG. 10 is a superior plan view of the talar component of FIG. 9;

FIG. 11 is a lateral side view of the talar component of FIG. 9;

FIG. 12 is a posterior view of the talar component of FIG. 9 as seen along line 12-12 of FIG. 10;

FIG. 13 is an anterior view of the talar component of FIG. 9 as seen along line 13-13 of FIG. 10;

Like reference numerals indicate the same or similar parts throughout the several figures.

A detailed description of the structures, features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE INVENTION

Figure 1:
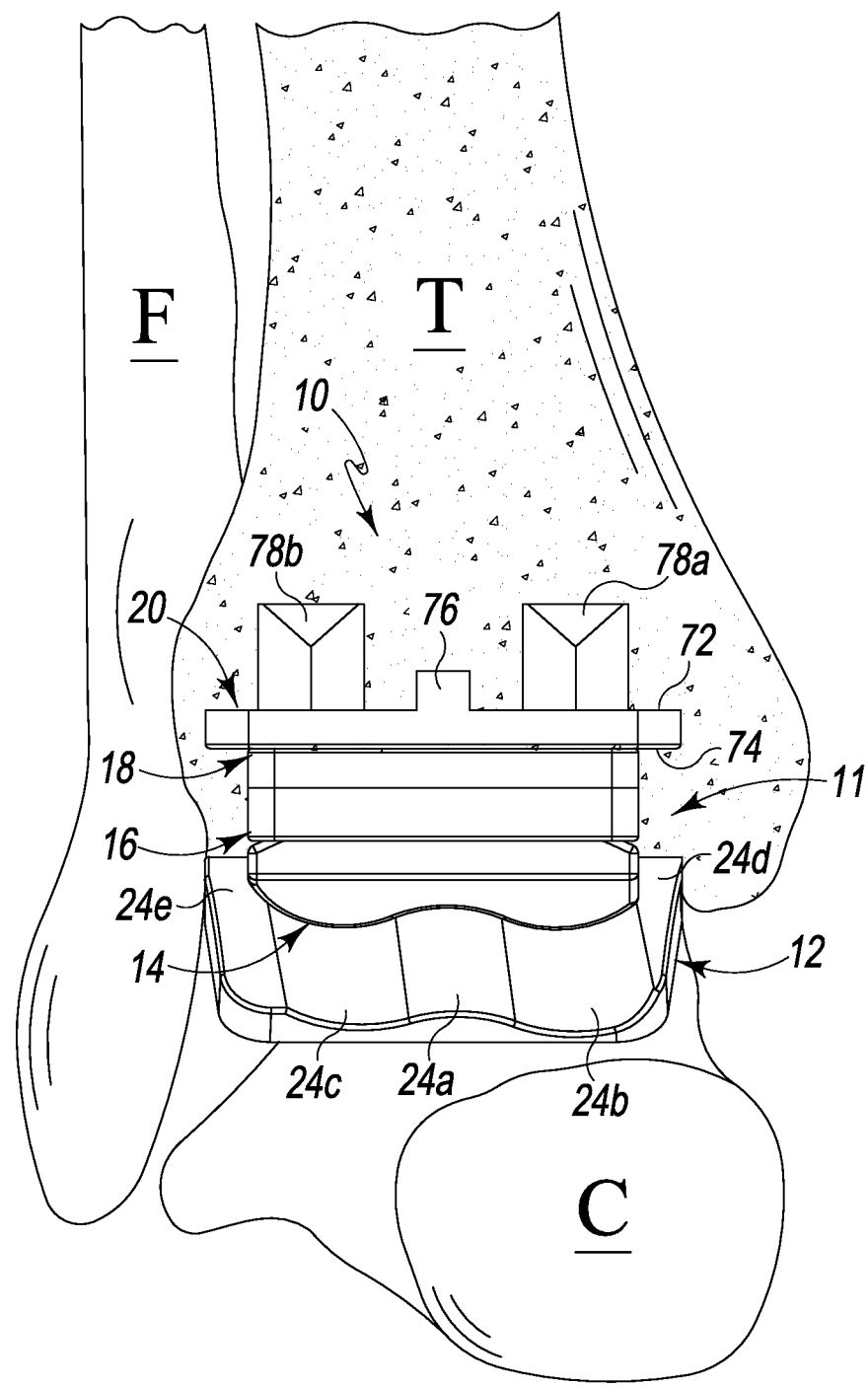
FIG. 1 is an anterior view of an ankle area of a right foot having a right ankle prosthesis according to the principles of the present invention implanted therein.

Referring to FIG. 1 there is depicted an anterior view of general bones of a human ankle/ankle area of a right foot (i.e. the tibia bone T, the fibula bone F and the calceneus bone C) in which an ankle prosthesis, generally designated 10, fashioned in accordance with the principles of the present invention, has been implanted. It should be understood that the talus bone of the ankle is not seen in FIG. 1 due to the ankle prosthesis 10 being implanted thereon. The ankle prosthesis 10 is an embodiment of a multi-axial dual mobile bearing prosthesis, as per the present principles, which is usable in various orthopedic prostheses for other parts of the body. However, the principles of the present invention will be described in connection with an ankle prosthesis. The ankle prosthesis 10 is a right ankle prosthesis since a portion thereof is fashioned for the right ankle as described herein. The ankle prosthesis can, of course, be made for a left ankle as is described herein.

The ankle prosthesis 10 has several components that interact to provide an ankle prosthesis which mimics a natural ankle joint (i.e. as between the tibia and the talus/calceneus). Particularly, as shown in exploded view in FIGS. 7 and 8, the ankle prosthesis 10 includes a talus or talar (hereinafter collectively, talar) component 12 that is configured for attachment to the talus or calceneus bone, a tibia or tibial (hereinafter collectively, tibial) component 20 that is configured for attachment to the tibia bone, and a dual bearing component 11 situated between the talar component 12 and the tibial component 20 that is configured to allow articulation or translation with respect to the talar component 20 and allow articulation or translation with respect to the tibial component 20, the details of which are described below. In short, the dual bearing component 11 interacts with the talar component 12 and the tibial component 20 to provide/allow multi-axial movement of the ankle prosthesis 10 and thus the reconstructed ankle joint.

The various components of the ankle prosthesis 10 are particularly shown in FIGS. 9-27 and in exploded views in FIGS. 7-8. Other figures (FIGS. 2-6 and 9-34) show the ankle prosthesis 10 in various views.

Figure 25:
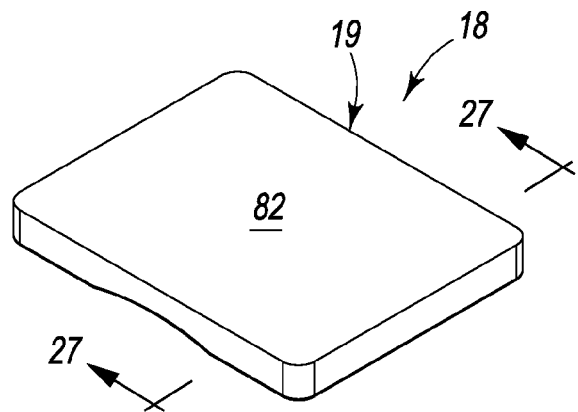
FIG. 25 is an isometric superior/lateral view of a superior bearing of the dual bearing component of the right ankle prosthesis of FIG. 1.
Figure 26:
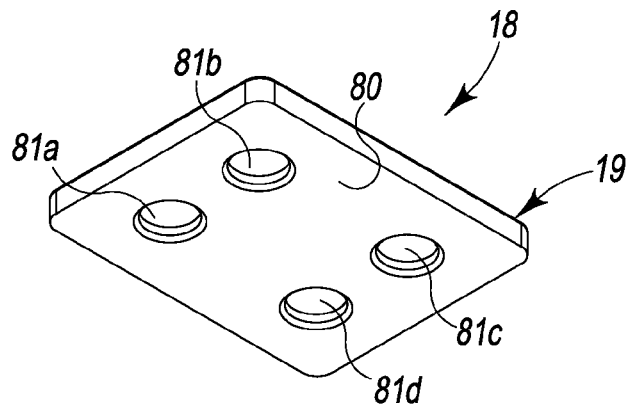
FIG. 26 is an isometric inferior/lateral view of the superior bearing of FIG. 25.
Figure 27:
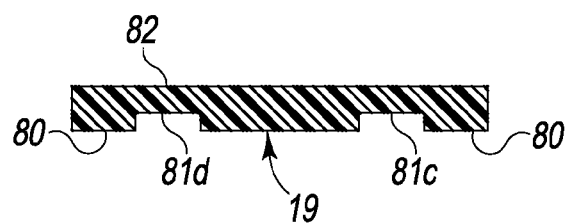
FIG. 27 is a sectional view of the superior bearing of FIG. 25 taken along line 27-27 thereof.
Figure 28:
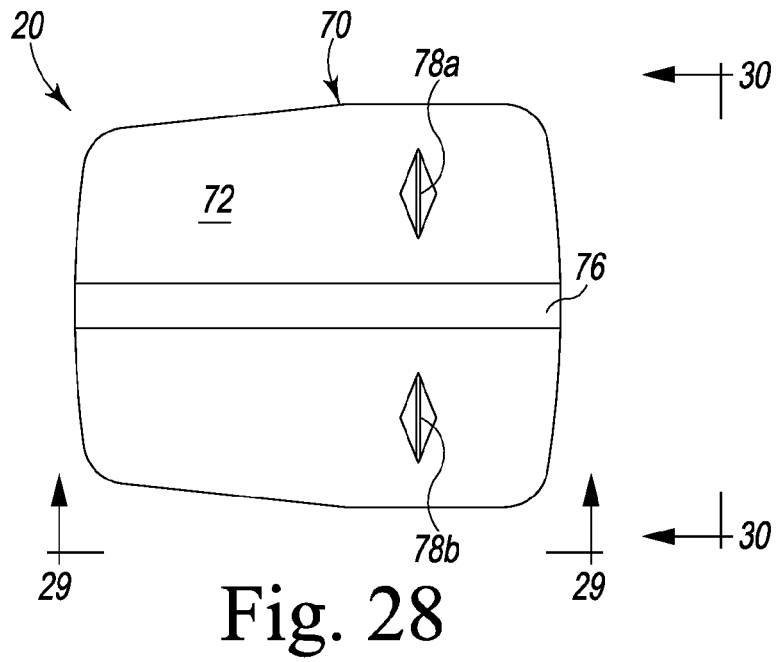
FIG. 28 is a superior plan view of a tibial component of the right ankle prosthesis of FIG. 1.
Figure 29:
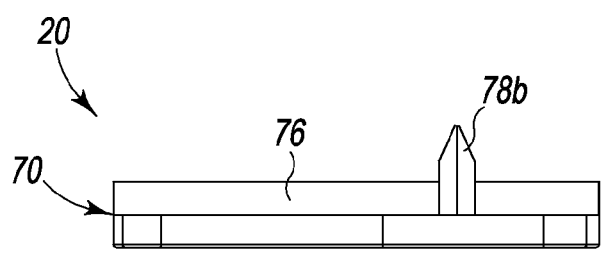
FIG. 29 is a lateral view of the tibial component of FIG. 28 as seen along line 29-29 of FIG. 28.
Figure 30:
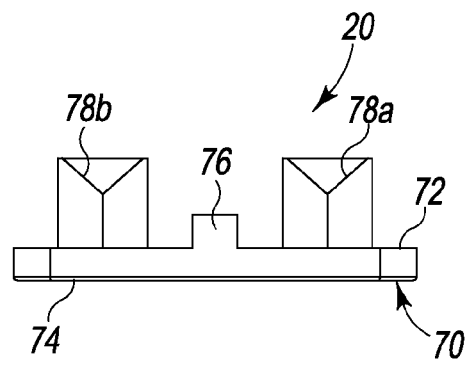
FIG. 30 is an anterior view of the tibial component of FIG. 28 as seen along line 30-30 of FIG. 30.

Referring to FIGS. 25-27, the tibial component 20 is shown in greater detail. The tibial component 20 includes a plate 70 and other features described herein, formed of a biocompatible metal such as stainless steel, titanium, an alloy of same, or other biocompatible material. The plate 70 is generally rectangular in shape except that it narrows slightly from the anterior side (i.e. the right side of FIG. 25) of the plate 70 to the posterior side (i.e. the left side of FIG. 25) of the plate 70. The plate 70 has a generally planar and smooth superior surface 72 and a generally planar and smooth inferior surface 74. Alternatively or additionally, the superior surface 72 may be textured, porous or otherwise if desired to promote bone ingrowth and/or have a slight convex or concave contour. The superior surface 72 has a ridge or projection 76 that extends from and between the anterior side and the posterior side of the plate 70. The ridge 76 is generally rectangular in cross section along its length and serves to prevent or guard against twisting after implantation. The ridge 76 may take shapes other than rectangular. Furthermore, the ridge 76 may not extend entirely from the posterior edge of the plate 70 to the anterior edge of the plate 70. Moreover, the ridge 76 may not be continuous but instead be comprises of two or more segments. Other configurations and arrangements are contemplated.

The superior surface 72 also has a first spike, stem, point or barb (hereinafter, spike) 78a situated on one side of the ridge 76 that extends in the superior direction and a second spike, stem, point or barb (hereinafter spike) 78b situated on another side of the ridge 76 that likewise extends in the superior direction, it being appreciated that the nomenclature first and second are arbitrary. The spikes 78a, 78b are situated proximate the anterior side of the plate 70 and are configured to extend into the tibia T in order to help retain the tibial component 20 onto the tibia and prevent and/or guard against twisting after implantation. The length of the spikes 78a, 78b are subject to variation. Preferably, but not necessarily, the tibial component 20 is machined or made from a single mass of the desired biocompatible material.

Referring to FIGS. 9-13, the talar component 12 is shown in greater detail. The talar component 12 includes a plate 22 formed of a biocompatible metal such as stainless steel, titanium, an alloy of same or other biocompatible material. The plate 22 is generally in the shape of an arc that mimics the articulation or translation arc of the natural human ankle joint. The plate 22 also narrows slightly from an anterior side (i.e. the right side of FIG. 25) of the plate 22 to the posterior side (i.e. the left side of FIG. 25) of the plate 22. The plate 22 has a smooth superior surface 24 with several contours extending from and between the anterior and posterior sides of the plate 22. As best discerned in FIGS. 9, 12 and 13, the superior surface has an intermediate convex contour 24a, a medial (i.e. the top right side of FIG. 9, the left side of FIG. 12, and the right side of FIG. 13) concave contour 24b and a lateral (i.e. the bottom left side of FIG. 9, the right side of FIG. 12, and the left side of FIG. 13) concave contour 24c. The medial side 27 of the plate 22 has an arced ledge 24d while the lateral side 26 of the plate 22 also has an arced ledge 24e. The arced ledge 24d supports and allows translation of a portion of the tibia T (see FIG. 1) thereon. The arched ledge 24e allows a portion of an inferior bearing 14 of the dual bearing component 11 to translate thereon.

As represented in FIG. 13 by the double-headed arrows and associated lines, the superior surface 24 of the plate 22 is angled upwardly from the medial side 27 to the lateral side 26 (or conversely angled downwardly from the lateral side 26 to the medial side 27) along the anterior to posterior arcuate length of the plate 22. In a preferred form, this angle is around 7.5° however, the angle may be more or less than 7.5°. The angle mimics the natural arch of the ankle.

Figure 5:
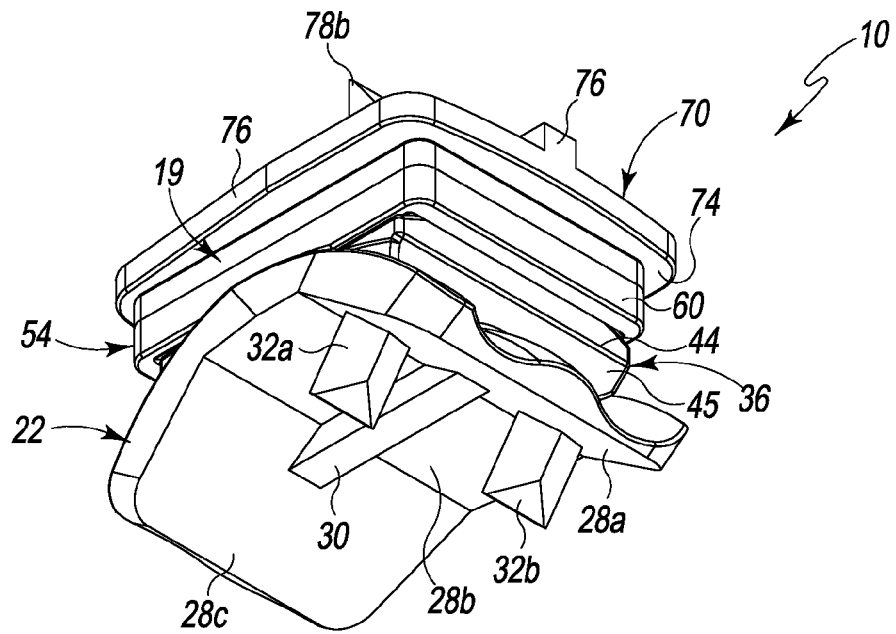
FIG. 5 is an isometric inferior/lateral view of the right ankle prosthesis of FIG. 1.
Figure 6:
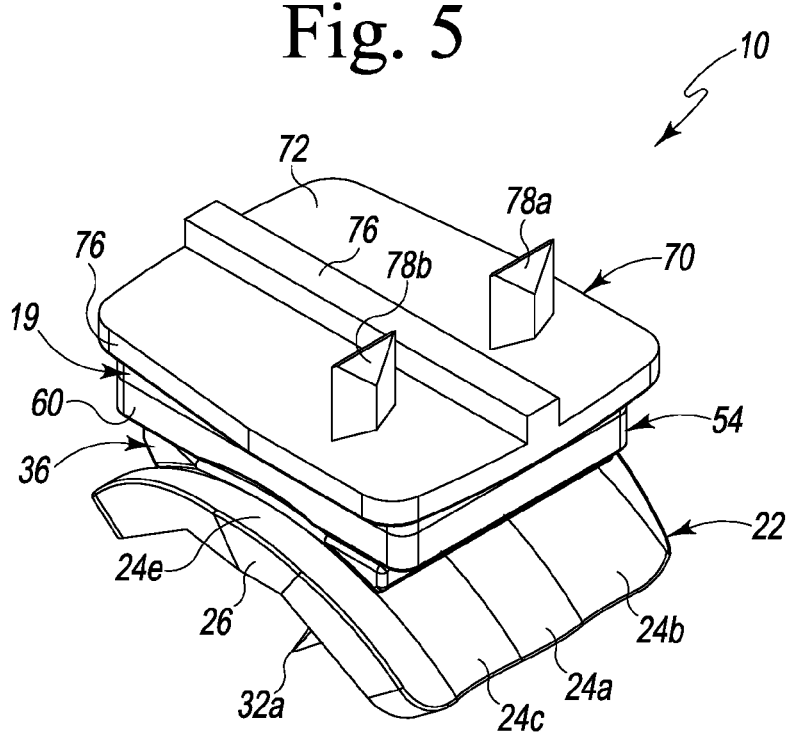
FIG. 6 is an isometric superior/lateral view of the right ankle prosthesis of FIG. 1.
Figure 14:
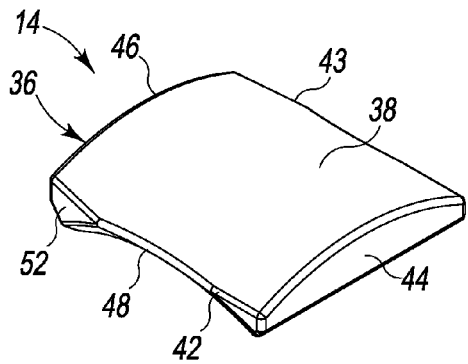
FIG. 14 is an isometric superior/lateral view of an inferior bearing of a dual bearing component of the right ankle prosthesis of FIG. 1.
Figure 15:
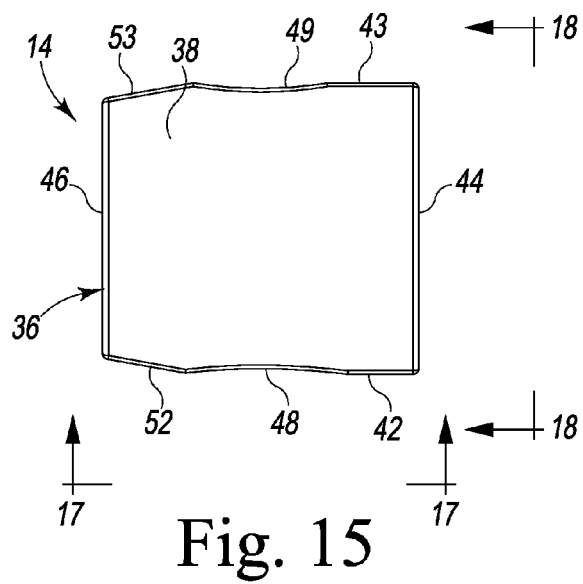
FIG. 15 is a superior plan view of the inferior bearing of FIG. 14.

With additional reference to FIGS. 5 and 7, the inferior surface 28 of the plate 22 has three generally planar and smooth arcuate sections or cuts 28a, 28b, 28c that together form the plate arch. These sections or cuts 28a, 28b, 28c correspond to the bone cuts in the prepared talar (or calceneal) bone. Alternatively or additionally, the inferior surface 28 may be textured, porous or otherwise if desired to promote bone ingrowth. A ridge or projection 30 extends from section 28b of the inferior surface 28 between section 28a and section 28c. The ridge 30 is generally rectangular in cross section along its length and serves to prevent or guard against twisting after implantation. The ridge 30 may take shapes other than rectangular. Section 28c of the inferior surface 28 also includes a first spike, stem, point or barb (hereinafter, spike) 32a situated on one side of the ridge 30 that extends in the inferior direction, and a second spike, stem, point or barb (hereinafter spike) 32b situated on another side of the ridge 30 that likewise extends in the inferior direction, it being appreciated that the nomenclature first and second are arbitrary. The spikes 32a, 32b are situated proximate the anterior side of the plate 22 and are configured to extend into the talus or calceneus bone in order to help retain the talar component 12 onto the talus or calceneus and prevent and/or guard against twisting after implantation. The length of the spikes 32a, 32b are subject to variation. Preferably, but not necessarily, the talar component 12 is machined or made from a single mass of the desired biocompatible material.

As shown in FIGS. 7 and 8, the dual bearing component 11 is composed of three parts; a bearing plate 16, an inferior bearing 14 and a superior bearing 18. The bearing plate 16 is particularly shown in FIGS. 19-24, the inferior bearing 14 in FIGS. 14-18, and the superior bearing in FIGS. 25-27.

Referring to FIGS. 19-24, the bearing plate 16 of the dual bearing component 11 is shown. The bearing plate 16 is defined by a plate 54 formed of a biocompatible metal such as stainless steel, titanium, an alloy of same or other biocompatible material. The plate 54 is generally in the shape of a rectangle and sized to fit under the tibial plate 70. A superior surface 56 of the plate 54 includes a plurality of projections 58a, 58b, 58c and 58d which extend in the superior direction. The projections 58a, 58b, 58c and 58d are depicted as circular tabs or cylinders but may take other shapes as desired. Moreover, while four (4) projections are shown, more or less projections may be provided. The projections 58a, 58b, 58c and 58d are preferably spaced on the superior surface 56 to provide secure connectivity to the superior bearing 18 as explained below.

Figure 24:
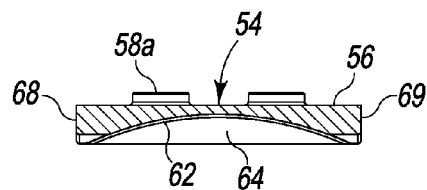
FIG. 24 is a sectional view of the bearing plate of FIG. 23 taken along line 24-24 thereof.

The plate 16 includes a rim 60 that extends about the periphery of the plate 16 and projects in the inferior direction. As best seen in FIG. 24, an inferior surface 62 of the plate is arced or curved from a medial side 68 of the plate 54 to a lateral side 69 of the plate 54 within the peripheral rim 60. As such, a generally arced anterior edge 63 is formed at the anterior end of the peripheral rim 60 and a generally arced posterior edge 64 is formed at the posterior end of the peripheral rim 60. The peripheral rim also has a first arced flat 66 at the medial side 68 and a second arced flat 67 at the lateral side 69. As described below, the curved inferior surface 62, the peripheral rim 60 and the anterior and posterior ends 63, 64 provide a pocket that receives the inferior bearing 14.

Referring to FIGS. 25-27, the superior bearing 18 of the dual bearing component 11 is shown. The superior bearing 18 is defined by a plate 19 formed of a biocompatible plastic such as polyethylene, polyetheretherketone (PEEK), polytetrafluoroethylene (PTFE), another biocompatible plastic, or other biocompatible material that provides a gliding bearing surface. The plate 54 is generally in the shape of a rectangle and sized to fit onto the superior surface 56 of the bearing plate 18. The plate 19 has a generally planar and smooth superior surface 82 and a generally planar and smooth inferior surface 80. The inferior surface 80 has a plurality of indentations 81a, 81b, 81c and 81d which extend in the inferior direction. The indentations 81a, 81b, 81c and 81d are depicted as circular bores or concavities to coincide with the shape of the projections 58a, 58b, 58c and 58d of the bearing component 16, but may take other shapes as desired as long as they coincide and/or cooperate with the projections 58a, 58b, 58c and 58d of the bearing component 16. Moreover, while four (4) indentations are shown, more or less indentations may be provided, again as long as they coincide and/or cooperate with the projections 58a, 58b, 58c and 58d of the bearing component 16. The indentations 81a, 81b, 81c and 81d are thus preferably spaced on the inferior surface 80 to coincide with the spacing of the projections 58a, 58b, 58c and 58d of the bearing component 16 to provide secure connectivity bearing component 16. The superior bearing 18 is bonded to the bearing plate 16.

Referring to FIGS. 14-18, the inferior bearing 14 of the dual bearing component 11 is shown. The inferior bearing 14 is defined by a plate 36 formed of a biocompatible plastic such as polyethylene, polyetheretherketone (PEEK), polytetrafluoroethylene (PTFE), another biocompatible plastic, or other biocompatible material that provides a gliding bearing surface. The plate 36 is generally in the shape of a rectangle but narrows slightly from the anterior side 44 (i.e. the right side of FIG. 15) of the plate 36 to the posterior side (i.e. the left side of FIG. 15) of the plate 36. A superior side 38 of the plate 36 is smooth and arced from a lateral side 42 to a medial side 43 thereof. The arc of the superior side 38 corresponds to the arc of the inferior side 62 of the bearing plate 54. Additionally, the lateral side 42 of the plate 36 has an arced cutout 48 proximate a middle of the lateral side 42 and an angled portion 52 that transitions to the posterior side 46 of the plate. The medial side 43 of the plate 36 has an arced cutout 49 proximate a middle of the medial side 43 and an angled portion 53 that transitions to the posterior side 46 of the plate 36. This shape corresponds to the shape of the rim 60 of the bearing plate 54.

Figure 16:
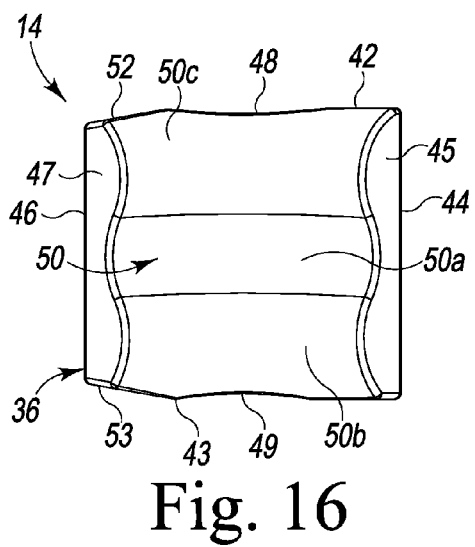
FIG. 16 is an inferior plan view of the inferior bearing of FIG. 14.
Figure 17:
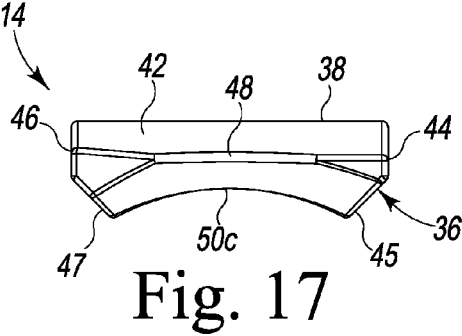
FIG. 17 is a lateral view of the inferior bearing of FIG. 14.
Figure 18:
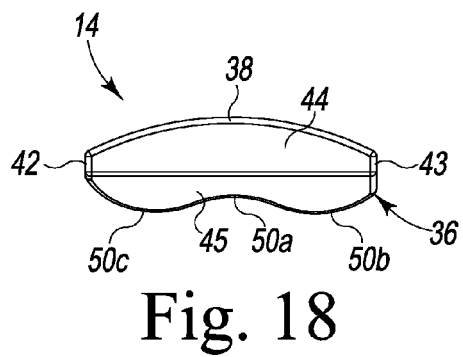
FIG. 18 is an anterior view of the inferior bearing of FIG. 14.
Figure 19:
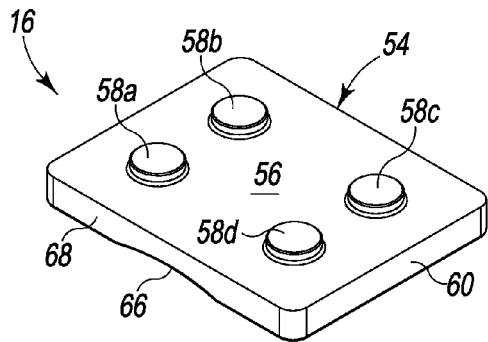
FIG. 19 is an isometric superior/lateral view of a bearing plate of the dual bearing component of the right ankle prosthesis of FIG. 1.
Figure 20:
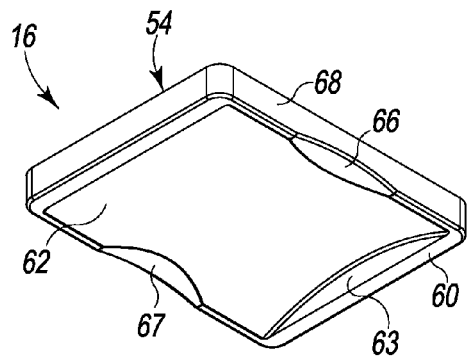
FIG. 20 is an isometric inferior/lateral view of the bearing plate of FIG. 19.
Figure 21:
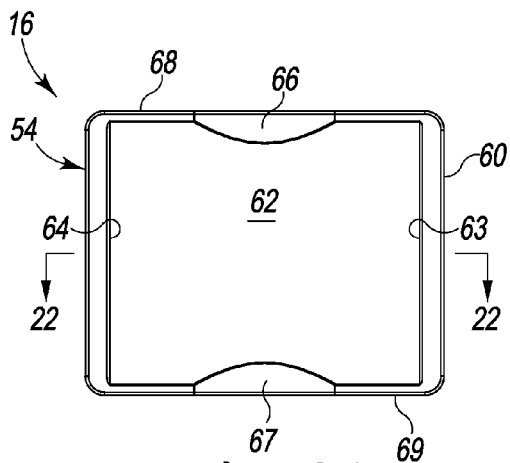
FIG. 21 is an inferior plan view of the bearing plate of FIG. 19.
Figure 22:
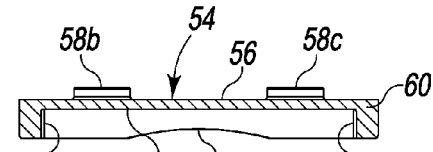
FIG. 22 is a sectional view of the bearing plate of FIG. 21 taken along line 22-22.
Figure 23:
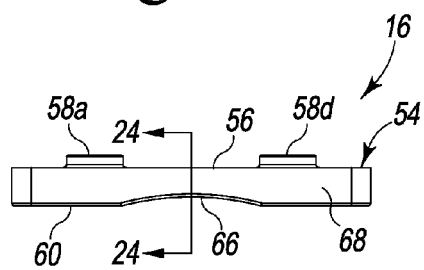
FIG. 23 is a lateral view of the bearing plate of FIG. 19.

The anterior side 44 of the plate 36 is generally arc shaped and corresponds to the arced anterior inside edge 63 of the bearing plate 54. Likewise, the posterior side 46 of the plate 36 is generally arc shaped and corresponds to the arced posterior inside edge 64 of the bearing plate 54. Moreover, as best seen in FIGS. 16 and 17, the anterior side 44 has a lower angle 45 that angles inwardly towards the inferior surface 50. Likewise, the posterior side 46 has a lower angle 47 that angles inwardly towards the inferior surface 50.

The curved and contoured superior surface of the talar component thus includes first and second sagital longitudinal concave grooves extending from the anterior side to the posterior side and a first sagital longitudinal convex ridge situated between the first and second sagital longitudinal concave grooves. A radius of the first and second sagital longitudinal concave grooves and of the first sagital longitudinal convex ridge vary with a minor arc existing laterally and becoming greater medially for anatomic-like tracking of the talar component relative to the inferior bearing.

Figure 4:
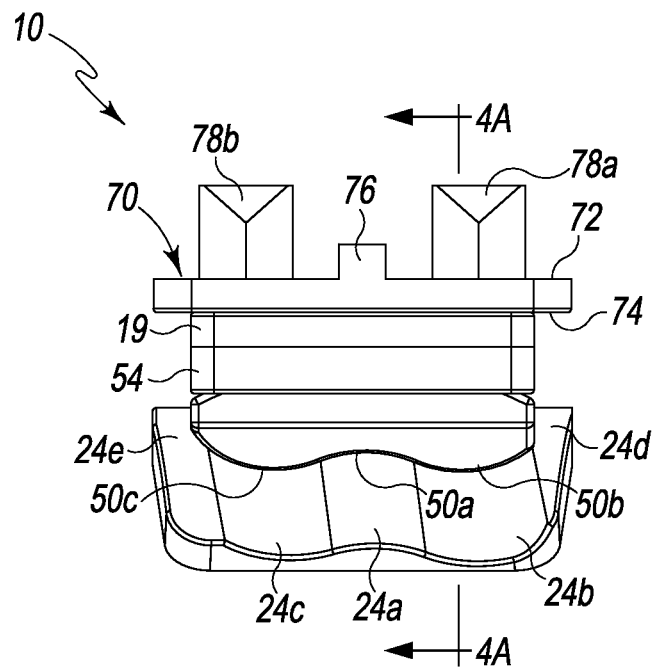
FIG. 4 is an anterior view of the right ankle prosthesis of FIG. 1.
Figure 4A:
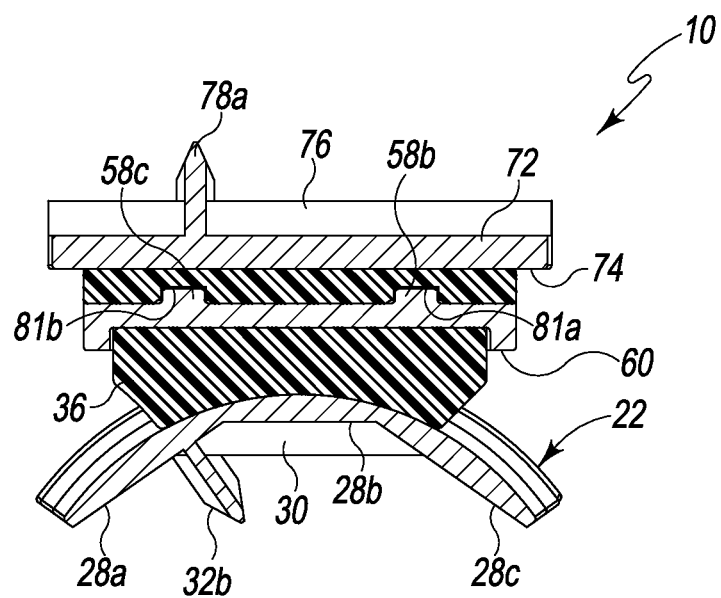
FIG. 4A is a sectional view of the right ankle prosthesis of FIG. 4 taken along line 4A-4A thereof (medial to lateral)
Figure 31:
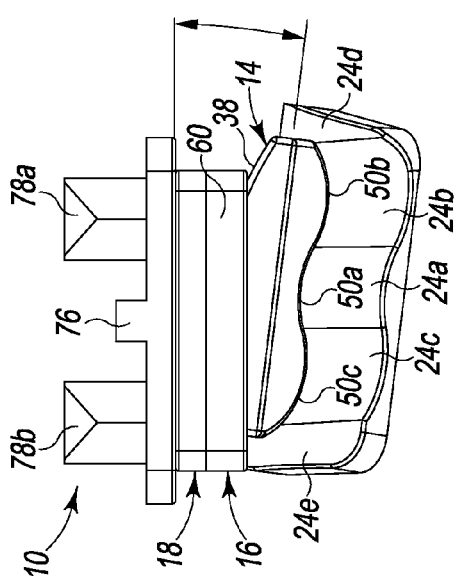
FIG. 31 is an anterior view of the right ankle prosthesis of FIG. 1 illustrating maximum eversion translation.
Figure 32:
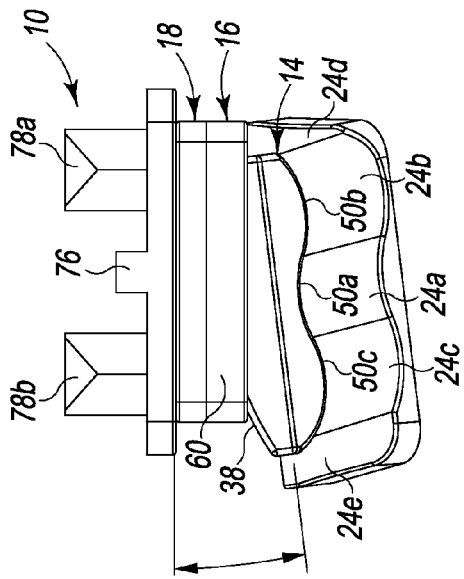
FIG. 32 is an anterior view of the right ankle prosthesis of FIG. 1 illustrating maximum inversion translation.

As best seen in FIG. 4A, the upper part of the plate 36 is thus sized to fit into the pocket or area formed by the curved inferior surface 62, the peripheral rim 60 and the anterior and posterior ends 63, 64 of the bearing plate 16. The inferior bearing plate 36, however, is not bonded to the bearing plate 18 but is free to translate in the medial/lateral directions relative to the bearing plate. This is illustrated in FIGS. 31 and 32 and described below. The lip 60 may be considered a tracking lip that extends inferiorly around the periphery of the bearing located in both the anterior and posterior aspects. The tracking lip 60 of the bearing component plate that catches, guides and prevents the inferior bearing from dislodging from the bearing component plate in the anterior and posterior directions.

Figure 2:
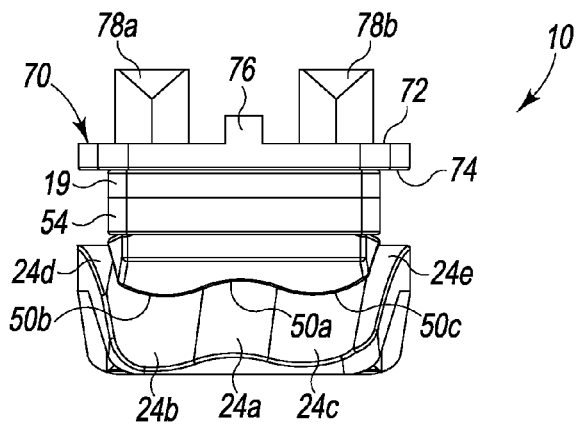
FIG. 2 is a posterior view of the right ankle prosthesis of FIG. 1.
Figure 3:
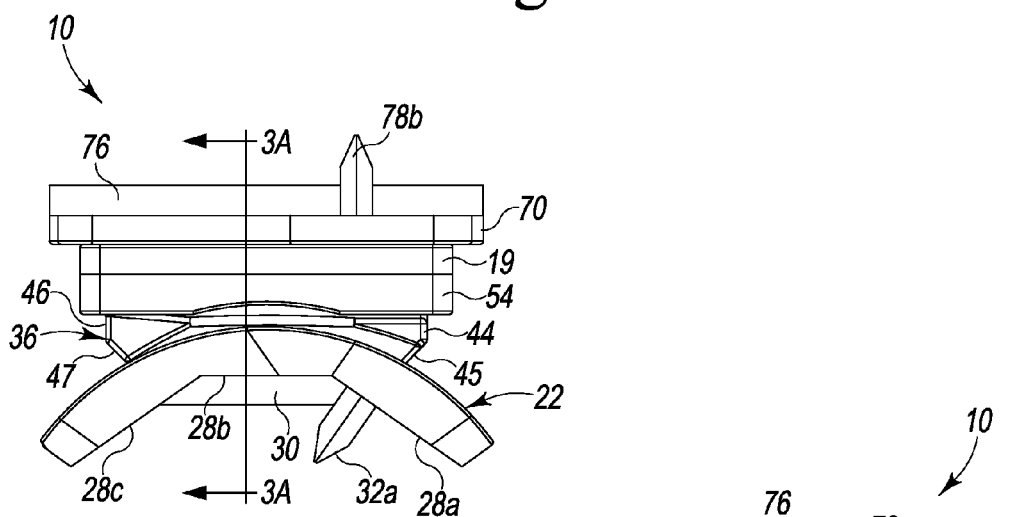
FIG. 3 is a lateral view of the right ankle prosthesis of FIG. 1.
Figure 3A:
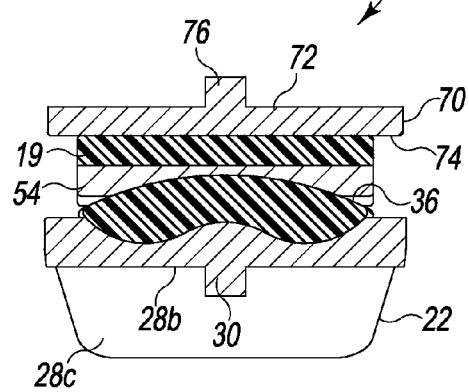
FIG. 3A is a sectional view of the right ankle prosthesis of FIG. 3 taken along line 3A-3A thereof (anterior to posterior)

The inferior surface 50 is generally smooth with several contours extending from and between the lower angle 45 of the anterior side 44 and the lower angle 47 of the posterior side 46 of the plate 54. As best discerned in FIGS. 16 and 18, the inferior surface 50 has an intermediate concave contour 50a, a medial (i.e. the bottom side of FIG. 16 and the right side of FIG. 18) convex contour 50b, and a lateral (i.e. the top side of FIG. 16 and the left side of FIG. 18) convex contour 50c. The contours 50a, 50c and 50b correspond oppositely to the contours 24a, 24b and 24c of the superior surface 24 of the talar plate 22. Particularly, as best seen in FIGS. 2 and 4, the contours 50a, 50b, 50c of the inferior bearing 14 fit into the contours 24a, 24b, 24c of the talar component 12. This allows translation or articulation between the talar component 12 and the inferior bearing 14. Such translation or articulation is shown with respect to FIGS. 33 and 34 described below.

With reference to FIGS. 31 and 32, the dual bearing component 11 thus provides a superior bearing surface for the tibial component 20 that allows articulation/translation of the dual bearing component 11 relative to the tibial component 20 in order to provide/allow eversion and inversion. As depicted in FIG. 31 and represented by the double-headed arrow, the dual bearing component 11 and the talar component 12 provide up to 7° of eversion relative to the tibial component 20. The tibial component 20 also slides about the superior bearing 18. This allows sideways movement of the foot.

Figure 33:
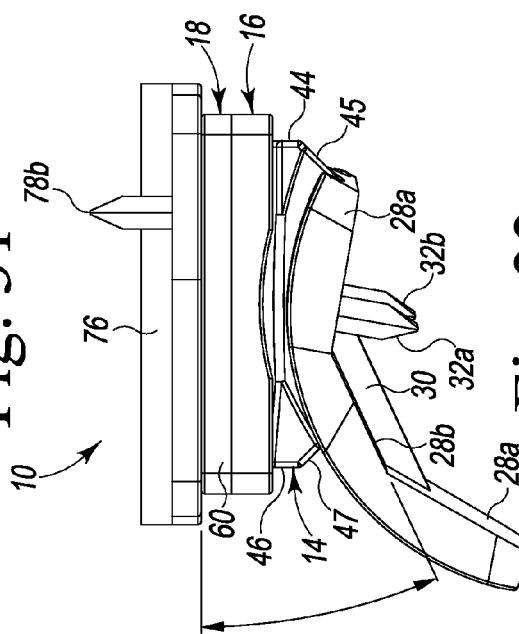
FIG. 33 is a lateral view of the right ankle prosthesis of FIG. 1 illustrating maximum dorsiflexion translation with respect to a pivot point of the talar component.
Figure 34:
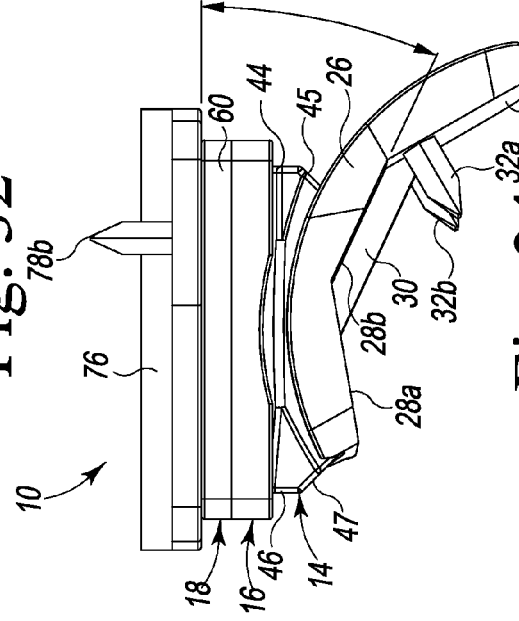
FIG. 34 is a lateral view of the right ankle prosthesis of FIG. 1 illustrating maximum plantarflexion translation with respect to a pivot point of the talar component.

With reference to FIGS. 33 and 34, the dual bearing component 11 thus provides an inferior bearing surface for the talar component 12 that allows articulation/translation of the talar component 12 relative to the dual bearing component 11 in order to provide/allow dorsiflexion and plantarflexion. As depicted in FIG. 33 and represented by the double-headed arrow, the talar component 12 provides up to 25° dorsiflexion relative to the pivot point (vertical centerline of the tibial component) for the talar plate 22. This allows up/down movement of the foot.

As indicated above, the present ankle prosthesis 10 is fashioned as an ankle prosthesis for the right foot. This is due to the curvature and superior sides of the talar component. As such, reversing the curvature and superior side of the talar plate allows the ankle prosthesis to be an ankle prosthesis for the left foot.

In a variation, the anterior to posterior fin 30 of the talar plate 22 may be slightly longer from posterior to anterior as shown in the figures and include two holes to accept two laterally placed locking screws. The two holes for the locking screws may be provided in two lateral flanges extending anterior to posterior in the inferior surface of the tibial component. Additionally, the anchoring stems or spikes of the talar plate 22 may be located in the anterior ⅓ of the inferior surface and slightly angled from superior/anterior to inferior/posterior.

In a variation, the tibial component 20 may have a lateral and dorsal flange to accept two locking fixation screws from lateral to medial across the superior surface of the tibial plate 70.

A method and system are provided that is used to prepare a bone surface for the implantation of a prosthesis fashioned in accordance with the present principles includes determining a location for a linear cut line on the bone surface and drilling a series of furrows tangent to the linear cut line to create an environment conducive to bone integration with the prosthesis.

With respect to the present ankle prosthesis, a method and system for implantation thereof includes the use of a lower extremity alignment guide, tibial and talar drill guides, tibial and talar saw guides, and tibial and talar broach guides, all components of which can be placed on and removed from multiple alignment anchor pins throughout the implantation procedure. Methods include an anterior implantation via an anterior implantation device, and a lateral to medial or medial to lateral implantation via a lateral to medial or medial to lateral implantation device. The methods include exposing the tibia and talus bones from the anterior (the anterior implantation method), from the lateral (or medial) side, resection of the tibia and talus bones, broaching the tibia and talus bones, and positioning and affixing the ankle joint prosthesis components.

It should be appreciated that although the present prosthesis, systems and methods set forth herein are described in detail in connection with the ankle joint, the prosthesis and/or principles of the present invention also has application for use with other joints throughout the body, such as for example, both the spine and wrist, with an upper or proximal fixation portion, a dual bearing design, and a lower or distal fixation component.

Moreover, while the invention has been illustrated and described in detail in the drawings and foregoing description, the same is to be considered as illustrative and not restrictive in character, and that all changes and modifications that come within the spirit of the invention are desired to be protected.

What is claimed is:

1. An ankle prosthesis comprising:
   a talar component;
   a tibial component; and
   a dual bearing component situated between the talar component and the tibial component, the dual bearing component having an inferior bearing and a superior bearing, the inferior bearing having an inferior contoured surface and a rounded arch from a medial to lateral side thereof, the superior bearing having a smooth superior surface;
   the talar component having an inferior surface configured for fixation to one of a talus bone or a calcaneal bone, and a superior, contoured surface configured complimentary to the inferior contoured surface of the inferior bearing so as to articulate with the inferior bearing, the superior surface of the talar component curved from an anterior side to a posterior side, and the curved and contoured superior surface of the talar component includes first and second sagital longitudinal concave grooves extending from the anterior side to the posterior side and a first sagital longitudinal convex ridge situated between the first and second sagital longitudinal concave grooves, a radius of the first and second sagital longitudinal concave grooves and of the first sagital longitudinal convex ridge varying with a minor arc existing laterally and becoming greater medially for anatomic-like tracking of the talar component relative to the inferior bearing the tibial component having an superior surface configured for fixation to a tibia bone or a fibula bone, and a smooth inferior surface that allows the smooth superior surface of the superior bearing to glide thereon to allow for rotational and translational movement relative thereto.

2. The ankle prosthesis of claim 1, wherein the talar component includes first and second anchoring stems on an anterior-most portion of the inferior surface thereof, and an anterior to posterior fin disposed on the inferior surface thereof.

3. The ankle prosthesis of claim 1, wherein the inferior surface of the inferior bearing is curved and slightly concave in an anterior to posterior direction.

4. The ankle prosthesis of claim 3, wherein the curved and slightly concave inferior surface of the inferior bearing is generally concave from one side of the inferior bearing to an opposite side of the inferior bearing.

5. The ankle prosthesis of claim 3, wherein the inferior surface of the inferior bearing has a smooth central groove, a smooth medial ridge, and a lateral ridge, each one extending from an anterior side to a posterior side thereof.

6. The ankle prosthesis of claim 1, wherein the superior surface of the inferior bearing is curved and slightly convex from the anterior side to the posterior side thereof.

7. The ankle prosthesis of claim 6, wherein the curved and slightly convex superior surface of the inferior bearing is generally convex from a medial side of the inferior bearing to a lateral side of the inferior bearing.

8. The ankle prosthesis of claim 1, wherein the inferior surface of the superior bearing is generally curved from a medial side to a lateral side thereof for motion in the frontal plane.

9. The ankle prosthesis of claim 1, wherein the superior surface of the tibial component is porous coated, and includes first and second anchoring stems and an anterior to posterior stabilizing fin situated between the first and second anchoring stems.

10. An ankle prosthesis comprising:
a talar component;
a tibial component;
a dual bearing component situated between the talar component and the tibial component, the dual bearing component having an inferior bearing and a superior bearing and a dual bearing component plate situated between the superior bearing and the inferior bearing, the inferior bearing having an inferior contoured surface and a rounded arch from a medial to lateral side thereof, the superior bearing having a smooth superior surface; wherein the superior bearing is affixed to the dual bearing component plate and the inferior bearing is free to translate relative to the dual bearing component plate.

11. The ankle prosthesis of claim 10, wherein the superior surface of the inferior bearing is curved from medial to lateral and an inferior surface of the dual bearing component plate is likewise curved from medial to lateral to allow for motion in the frontal plane.

12. The ankle prosthesis of claim 11, wherein the dual bearing component plate has an inferior peripheral lip at both an anterior edge of the dual bearing component plate and a posterior edge of the dual bearing component plate that catches, guides and prevents the inferior bearing from dislodging therefrom in the anterior and posterior directions.

13. An ankle prosthesis comprising:
a talar component having an inferior surface configured for fixation to one of a talus bone or a calcaneal bone and a superior contoured surface;
a tibial component having a superior surface configured for fixation to a tibia bone or a fibula bone and a smooth inferior surface;
a dual bearing component disposed between the talar component and the tibial component, the dual bearing component comprising:
a bearing component plate having a superior surface and an inferior surface;
a superior bearing affixed to the superior surface of the bearing component plate and having a smooth superior surface that allows the smooth inferior surface of the tibial component to glide thereon allowing rotational and translational movement between the superior bearing and the tibial component; and
an inferior bearing free floating with respect to the inferior surface of the bearing component plate and having an inferior contoured surface configured complimentary to the superior contoured surface of the talar component so as to allow articulation between the inferior contoured surface and the talar component, wherein the superior surface of the bearing component plate has a plurality of projections and the inferior surface of the superior bearing has a plurality of indentions corresponding in number and placement to the plurality of projections.

14. The ankle prosthesis of claim 13, wherein the superior surface of the talar component is curved from an anterior side to a posterior side.

15. The ankle prosthesis of claim 14, wherein the curved superior surface of the talar component is generally convex from the anterior side to the posterior side.

16. The ankle prosthesis of claim 14, wherein the curved and contoured superior surface of the talar component includes first and second sagital longitudinal concave grooves extending from the anterior side to the posterior side and a first sagital longitudinal convex ridge situated between the first and second sagital longitudinal concave grooves, a radius of the first and second sagital longitudinal concave grooves and of the first sagital longitudinal convex ridge varying with a minor arc existing laterally and becoming greater medially for anatomic-like tracking of the talar component relative to the inferior bearing.

17. The ankle prosthesis of claim 13, wherein the inferior surface of the talar component is semi-curved through three angled and adjoined surfaces extending from the anterior side to the posterior side creating an arch from anterior to posterior.

18. The ankle prosthesis of claim 17, wherein the inferior surface of the talar component is porous coated.

19. The ankle prosthesis of claim 17, wherein each one of the three adjoined surfaces of the inferior surface of the talar component creating the arch are flat.

20. The ankle prosthesis of claim 13, wherein the talar component includes first and second anchoring stems on the inferior surface thereof, and an anterior to posterior fin disposed on the inferior surface thereof and between the first and second anchoring stems.

21. An ankle prosthesis comprising:
a talar component having an inferior surface configured for fixation to one of a talus bone or a calcaneal bone and a superior contoured surface;
a tibial component having a superior surface configured for fixation to a tibia bone or a fibula bone and a smooth inferior surface; and
a dual bearing component disposed between the talar component and the tibial component, the dual bearing component comprising:
a bearing component plate having a superior surface and an inferior surface;
a superior bearing affixed to the superior surface of the bearing component plate and having a smooth superior surface that allows the smooth inferior surface of the tibial component to glide thereon allowing rotational and translational movement between the superior bearing and the tibial component; and
an inferior bearing free floating with respect to the inferior surface of the bearing component plate and having an inferior contoured surface configured complimentary to the superior contoured surface of the talar component so as to allow articulation between the inferior contoured surface and the talar component, wherein the inferior surface of the inferior bearing is curved and slightly concave in an anterior to posterior direction.

22. The ankle prosthesis of claim 21, wherein the curved and slightly concave inferior surface of the inferior bearing is generally concave from one side of the inferior bearing to an opposite side of the inferior bearing.

23. The ankle prosthesis of claim 21, wherein the inferior surface of the inferior bearing has a smooth central groove, a smooth medial ridge, and a lateral ridge, each one extending from an anterior side to a posterior side thereof.

24. An ankle prosthesis comprising:
a talar component having an inferior surface configured for fixation to one of a talus bone or a calcaneal bone and a superior contoured surface;
a tibial component having a superior surface configured for fixation to a tibia bone or a fibula bone and a smooth inferior surface; and
a dual bearing component disposed between the talar component and the tibial component, the dual bearing component comprising:
a bearing component plate having a superior surface and an inferior surface;
a superior bearing affixed to the superior surface of the bearing component plate and having a smooth superior surface that allows the smooth inferior surface of the tibial component to glide thereon allowing rotational and translational movement between the superior bearing and the tibial component; and
an inferior bearing free floating with respect to the inferior surface of the bearing component plate and having an inferior contoured surface configured complimentary to the superior contoured surface of the talar component so as to allow articulation between the inferior contoured surface and the talar component, wherein the superior surface of the inferior bearing is curved and slightly convex from the anterior side to the posterior side thereof.

25. The ankle prosthesis of claim 24, wherein the curved and slightly convex superior surface of the inferior bearing is generally convex from a medial side of the inferior bearing to a lateral side of the inferior bearing.

26. The ankle prosthesis of claim 24, wherein the inferior surface of the superior bearing is generally curved from a medial side to a lateral side thereof for motion in the frontal plane.

27. The ankle prosthesis of claim 24, wherein the superior surface of the tibial component is porous coated, and includes first and second anchoring stems on an anterior most area of the superior surface and an anterior to posterior stabilizing fin between the first and second anchoring stems.

28. An ankle prosthesis comprising:
a talar component having an inferior surface configured for fixation to one of a talus bone or a calcaneal bone and a superior contoured surface;
a tibial component having a superior surface configured for fixation to a tibia bone or a fibula bone and a smooth inferior surface; and
a dual bearing component disposed between the talar component and the tibial component, the dual bearing component comprising:
a bearing component plate having a superior surface and an inferior surface;
a superior bearing affixed to the superior surface of the bearing component plate and having a smooth superior surface that allows the smooth inferior surface of the tibial component to glide thereon allowing rotational and translational movement between the superior bearing and the tibial component; and
an inferior bearing free floating with respect to the inferior surface of the bearing component plate and having an inferior contoured surface configured complimentary to the superior contoured surface of the talar component so as to allow articulation between the inferior contoured surface and the talar component, wherein the superior bearing is affixed to the bearing component plate and the inferior bearing is free to translate relative to the bearing component plate.

29. The ankle prosthesis of claim 28, wherein the superior surface of the inferior bearing is curved from medial to lateral and an inferior surface of the bearing component plate is likewise curved from medial to lateral to allow for motion in the frontal plane.

30. The ankle prosthesis of claim 29, wherein the bearing component plate has an inferior peripheral lip at both an anterior edge of the bearing component plate and a posterior edge of the bearing component plate that catches, guides and prevents the inferior bearing from dislodging therefrom in the anterior and posterior directions.

* * * * *